United States Patent
Hayashida et al.

(10) Patent No.: US 9,693,965 B2
(45) Date of Patent: Jul. 4, 2017

(54) FUNCTIONAL POLYMER FILM-COATED PARTICLE HAVING HIGH DRUG CONTENT, TABLET CONTAINING SAME, AND METHODS FOR PRODUCTION THEREOF

(71) Applicants: ZENSEI PHARMACEUTICAL INDUSTRIES CO., LTD., Osaka (JP); POWREX CORPORATION, Hyogo (JP)

(72) Inventors: Tomohiro Hayashida, Osaka (JP); Junji Yamazaki, Osaka (JP); Yoshio Nakano, Osaka (JP); Masaya Hizaki, Osaka (JP); Naotoshi Kinoshita, Hyogo (JP)

(73) Assignees: POWEREX CORPORATION, Hyogo (JP); ZENSEI PHARMACUETICAL INDUSTRIES CO., LTD., Osaka (JP)

( * ) Notice: Subject to any disclaimer, the term of this patent is extended or adjusted under 35 U.S.C. 154(b) by 0 days.

(21) Appl. No.: 14/889,657

(22) PCT Filed: May 8, 2013

(86) PCT No.: PCT/JP2013/062890
§ 371 (c)(1),
(2) Date: Nov. 6, 2015

(87) PCT Pub. No.: WO2014/181390
PCT Pub. Date: Nov. 13, 2014

(65) Prior Publication Data
US 2016/0120813 A1 May 5, 2016

(51) Int. Cl.
*A61K 9/14* (2006.01)
*A61K 9/48* (2006.01)
(Continued)

(52) U.S. Cl.
CPC .......... *A61K 9/4816* (2013.01); *A61K 9/0056* (2013.01); *A61K 9/14* (2013.01);
(Continued)

(58) Field of Classification Search
CPC .......... A61K 9/14; A61K 47/32; A61K 47/38; A61L 9/20
See application file for complete search history.

(56) References Cited

U.S. PATENT DOCUMENTS 7,875,292 B2    1/2011   Shimizu
2004/0253309 A1  12/2004  Tanijiri
(Continued)

FOREIGN PATENT DOCUMENTS

JP    2005-23058 A  *  1/2005
JP    2005023058 A     1/2005
(Continued)

OTHER PUBLICATIONS

Takayuki, Kamata et al. Society of Powder Technology, [2000], vol. 1999, Shukigo, pp. 149-153. (English Translation submitted herewith, honoring the previously filed document and our statement that the English Translation of said document would be forthcoming).
(Continued)

*Primary Examiner* — Carlos Azpuru
(74) *Attorney, Agent, or Firm* — Millen, White, Zelano and Branigan, P.C.

(57) ABSTRACT

Provided are functional drug-containing particles which can be compressed into tablets and in particular, to orally disintegrating tablets by employing any of a dry molding method, a wet molding method, or a humidifying drying method. The functional drug-containing particles comprise substantially spherical drug-containing particles essentially including drug and a binder, the functional drug-containing particles including a functional polymer film selected from
(Continued)

the group consisting of an enteric film, a release control film, and a bitter taste masking film, an average particle diameter of said functional drug-containing particles being 400 μm or less, a particle diameter ratio $D_{90}/D_{10}$ of the functional drug-containing particles with respect to particle size distribution calculated on a volumetric basis being 1.65 or more, or a coefficient of variation in particle diameters being 24% or more.

17 Claims, 3 Drawing Sheets

(51) Int. Cl.
- *A61K 9/20* (2006.01)
- *A61K 31/137* (2006.01)
- *A61K 31/522* (2006.01)
- *A61K 9/00* (2006.01)
- *A61K 9/50* (2006.01)
- *B01J 2/00* (2006.01)
- *B01J 2/16* (2006.01)
- *A61K 9/16* (2006.01)

(52) U.S. Cl.
CPC ............ *A61K 9/167* (2013.01); *A61K 9/1652* (2013.01); *A61K 9/20* (2013.01); *A61K 9/2081* (2013.01); *A61K 9/2095* (2013.01); *A61K 9/5015* (2013.01); *A61K 9/5026* (2013.01); *A61K 9/5047* (2013.01); *A61K 9/5073* (2013.01); *A61K 31/137* (2013.01); *A61K 31/522* (2013.01); *B01J 2/003* (2013.01); *B01J 2/16* (2013.01)

(56) References Cited

U.S. PATENT DOCUMENTS

| | | | |
|---|---|---|---|
| 2009/0099154 A1 | | 4/2009 | Jain et al. |
| 2010/0015239 A1 | | 1/2010 | Ahmed |

FOREIGN PATENT DOCUMENTS

| | | | | |
|---|---|---|---|---|
| JP | 03746167 | B2 | | 2/2006 |
| JP | 2008013480 | A | | 1/2008 |
| JP | 2009-500318 | A | * | 1/2009 |
| JP | 2009500318 | A | | 1/2009 |
| JP | 2011-251959 | A | * | 12/2011 |
| JP | 2011251959 | A | | 12/2011 |
| JP | 2012240917 | A | | 12/2012 |
| WO | 2004066991 | A1 | | 8/2004 |
| WO | 2011/040195 | | * | 4/2011 |
| WO | 2011040195 | A1 | | 4/2011 |

OTHER PUBLICATIONS

International Search Report from PCT/JP2013/062890 dated Aug. 6, 2013.
Takayuki, Kamata et al. Society of Powder Technology, [2000], vol. 1999, Shukigo, pp. 149-153. (English Translation will be provided forthwith).
Search Opinion in corresponding EP application 13884151.5 dated Aug. 31, 2016.
Supplementary Search report in corresponding EP application 13884151.5 dated Aug. 31, 2016.
Machine english Translation of JP2012240917A published Dec. 10, 2012 to Zensei Yakuhin Kogyo KK.

\* cited by examiner

FUNCTIONAL POLYMER FILM-COATED PARTICLE HAVING HIGH DRUG CONTENT, TABLET CONTAINING SAME, AND METHODS FOR PRODUCTION THEREOF

TECHNICAL FIELD

The present invention relates to high-content drug particles coated with a functional polymer film, and a tablet including the high-content drug particles, and in particular, to an orally disintegrating tablet. Further, the present invention relates to a method for manufacturing such high-content drug particles and to a method for manufacturing the tablet including the high-content drug particles.

BACKGROUND ART

In recent years, the importance of improving patient compliance has been advocated, and for the purposes of allowing a patient whose ability of swallowing is weak, such as the elderly and an infant, to easily take medicine without water and of alleviating the burden of medicine administration care imposed on health care professionals, for example, by enabling a simplified suspension drug administration method, development and research of, for example, an orally disintegrating tablet which rapidly disintegrates in the oral cavity and when inputted into water, quickly disintegrates and disperses therein have been actively conducted.

As the methods for manufacturing the orally disintegrating tablet, there are three methods: as the first generation method, the so-called liquid drying method in which the orally disintegrating tablet is manufactured by pouring a drug and additive agent dispersed solution into a mold such as a blister pocket and drying is conducted; as the second generation method, the so-called wet molding method in which components constituted of drug and saccharides are formed into a wet lump, the wet lump is subjected to tableting molding at a low pressure, and thereafter, the resultant is dried; and as the third generation method, the so-called dry compression method in which the orally disintegrating tablet is manufactured by using an ordinary tableting apparatus by means of causing the functionality of a disintegrating tablet to develop through the selection of additives and elaborate formulation. Still now, many products are supplied by employing these tableting methods.

As the orally disintegrating tablets which have been so far marketed, there are many kinds of orally disintegrating tablets: such as the orally disintegrating tablet which has the very ordinary disintegrability and solubility; the orally disintegrating tablet which is manufactured by compounding drug particles prepared by directly coating drug itself with a bitter taste masking film; and the orally disintegrating tablet which is manufactured by compounding functional spherical fine particles, which are produced by preparing core fine particles prepared by layering drug to core particles and by coating the outer layers of the core fine particles with a release control film, an enteric film, or a bitter taste masking film.

Among the above-mentioned orally disintegrating tablets, in the case of the orally disintegrating tablet which is manufactured by producing the core fine particles prepared by layering the drug to the core particles, coating the outer layers of the core fine particles with the film having the functionality of the release control, the enteric coat, or the bitter taste masking, adding at least an excipient and a disintegrant to the coated particles obtained as mentioned above, and subjecting the resultant to compression molding, if the content of drug contained in one tablet is large, the tablet becomes large, thereby making it difficult to take the tablet. This is because the amount of the components, other than the drug, such as the core particles and the polymeric material forming the film inevitably becomes large.

Japanese Patent No. 3746167 discloses a granulated substance used for an orally disintegrating tablet, which is produced by layering an acid-unstable benzimidazole-based drug, for example, a mixture of lansoprazole and basic inorganic salt to core particles constituted of crystalline cellulose and lactose and further applying enteric coating thereto.

International Publication No. WO 2004/066991 discloses a method for manufacturing enteric sustained-release fine particles used for an orally disintegrating tablet, which includes the steps of: spraying a solution of hydroxypropyl methylcellulose, which contains tamsulosin hydrochloride, to core particles of crystalline cellulose or the like, thereby conducting layering; subsequently, applying sustained-release coating thereonto; and subsequently applying enteric coating thereonto.

Japanese Patent Application Laid-Open Publication No. 2012-240917 discloses fine particles used for manufacturing an orally disintegrating tablet which can be obtained by layering a coating liquid, prepared by adding drug in the form of acid addition salt and an inorganic or organic base to a water-soluble polymer solution, to spherical granules of crystalline cellulose; drying the resultant; and thereafter, applying a water-insoluble but water-permeable film thereonto. Although the water-insoluble water-permeable film coated onto the outermost layers of these fine particles suppresses diffusion and dissolution of the basic drug in the oral cavity, the water-insoluble water-permeable film is torn in the stomach or the upper part of the small intestine and the drug is released from the fine particles. Accordingly, in a case where these fine particles are used for manufacturing the orally disintegrating tablet, since the drug is not released in the oral cavity, the film applied onto the fine particles serves as a functional film which masks unpleasant taste of the drug.

Each of these particles obtained by layering the drug to the core particles of the crystalline cellulose or the like and further applying the functional film thereonto has a three-layer structure including at least a core particle in the center, a drug layer thereoutside, and the functional polymer layer further thereoutside, and thus, the particle diameter thereof inevitably becomes large.

In addition, a shape of each of the functional drug particles in the conventional technology, which have the core particles, depends on a shape of each of the core particles in the center and is thereby substantially spherical, and particle size distribution is comparatively narrow. Therefore, moldability into the tablet is inferior, and in order to manufacture a tablet having a hardness which can withstand the distribution in the market, it is required to increase a ratio of an excipient which allows easy molding.

CITATION LIST

Patent Literature

[Patent Literature 1] Japanese Patent No. 3746167
[Patent Literature 2] International Publication No. WO2004/066991

[Patent Literature 3] Japanese Patent Application Laid-Open Publication No. 2012-240917

SUMMARY OF THE INVENTION

Technical Problem

As discussed above, in order to increase the whole drug content, it is required for a particle diameter of each of the functional drug particles manufactured by the conventional technology to be made large. Thus, one of the problems to be solved by the present invention is to provide functional drug particles whose each drug content are large but whose each particle diameter is smaller than that of each of the particles manufactured by the conventional technology and a method for manufacturing the functional drug particles.

In addition, since the moldability into the tablet of the functional drug particles by the conventional technology is low, in order to manufacture a tablet having a hardness which can withstand the distribution in the market, a comparatively large amount of an excipient whose moldability is high is required. Thus, another problem to be solved by the present invention is to provide functional drug particles which do not need a large amount of the excipient having high moldability, unlike in the manufacturing of the particles by the conventional technology and whose moldability is high and a method for manufacturing a tablet and in particular, an orally disintegrating tablet by using these functional drug particles.

Solution to Problem

To obtain functional drug particles whose drug content is high as a whole, it is required for a drug content of drug particles before the application of a functional polymer film thereto (these are referred to as "bare particles") to be high. Therefore, according to the present invention, the bare particles do not contain core particles of crystalline cellulose or the like, used in the conventional technology. Instead, the bare particles are essentially constituted of drug and a binder, and therefore, particles whose drug content is 70% by weight or more can be prepared. These bare particles are prepared by using a spray drying fluidized bed granulation apparatus and are prepared from a solution of the binder in which the drug is dissolved or suspended. When the binder solution containing the drug is sprayed to this apparatus and is caused to collide with a high-temperature air flow which flows mist into the apparatus, the mist is instantaneously dried, becomes initial fine particles constituted of the drug and the binder, and forms a fluidized bed. When the spraying of the binder solution containing the drug is further continued, the initial fine particles are layered with the drug and the binder and grow into bare particles whose each particle diameter is comparatively large. On the other hand, new initial fine particles are sequentially formed from a part of the mist, and the growing by the layering of the drug and the binder starts in a delayed manner. Therefore, particle size distribution of the bare particles produced by this process becomes broad, as compared with that of the bare particles in the conventional technology which are formed by applying the layering around spherical-shaped core particles.

A polymer film for imparting the functionality of a sustained release property, an enteric property, a bitter taste masking property, or the like is applied to the bare particles essentially constituted of the drug and the binder, which are produced as described above, whereby functional drug-containing particles according to the present invention are provided.

The functional drug-containing particles according to the present invention allow a drug content to be made high and a particle diameter to be made small, as compared with those of the functional drug particles in the conventional technology. For example, the drug content can be 40% by weight or more and an average particle diameter can be 400 μm or less, thereby allowing miniaturization.

Further, the particle size distribution of the functional drug-containing particles according to the present invention is broad, as compared with that of the functional drug-containing particles in the conventional technology. This is because, as described above, the bare particles whose particle size distribution is broad due to the differences in the degrees of growing are used. Therefore, with respect to the particle size distribution of the functional drug-containing particles according to the present invention, that is, the bare particles coated with the functional polymer, a particle diameter ratio $D_{90}/D_{10}$ calculated on a volumetric basis is 1.65 or more in general, or a coefficient of variation in the particle diameters is 24% or more in general. Here, the "particle diameter ratio $D_{90}/D_{10}$" means a ratio of a particle diameter at 90% accumulation and a particle diameter at 10% accumulation, from the fine particle side, of accumulated particle sizes calculated on a volumetric basis, and the "coefficient of variation in the particle diameters" is a value obtained by measuring particle diameters by using a laser diffraction/scattering type particle diameter distribution measuring apparatus, which are then calculated on a volumetric basis, and by dividing an arithmetic standard deviation of the particle diameters by the average particle diameter, the value being expressed by %.

As described above, since the functional drug-containing particles according to the present invention has the broader particle size distribution than that of the conventional technology and has no hard core particles each in the center, the moldability into the tablet is higher than that of the conventional technology. Therefore, even when the amount of the excipient whose moldability is high is reduced and a ratio of the functional drug-containing particles is 50% to 90% of the total weight of a tablet, it is made possible to manufacture a tablet having a degree of a hardness which allows the tablet to withstand the distribution in the market and in particular, an orally disintegrating tablet through compression molding. As tableting methods in this case, any of the below described methods (i) to (iii) can be adopted:

(i) a commonly used tableting method in which at least a disintegrant and a lubricant are added to functional drug particles, and the resultant mixture is subjected to compression molding (dry compression method);

(ii) a wet molding method in which an aqueous solution including a binder and a saccharide or sugar alcohol is added to functional drug particles, the resultant is kneaded, the wet kneaded substance is molded at a low pressure into a tablet, and thereafter, the tablet is dried; or (iii) a humidifying drying method in which functional drug particles are mixed or coated with a saccharide or sugar alcohol which can be amorphous, thereafter, the resultant is compressed at a low pressure by employing a dry compression method into a tablet, the tablet is once humidified and then the humidified tablet is dried, in order to enhance the hardness.

DESCRIPTION OF EMBODIMENTS

Process 1: Production of Core Fine Particles (Bare Particles)

Drug which can be used in the present invention is not limited as far as the drug is orally administered. However, when the drug is compressed into an orally disintegrating tablet, suitable is drug which requires the provision of the functionality of a bitter taste masking property, an enteric property, and/or a sustained release property for disintegrated particles, or to which preferably, the functionality of these is provided.

A liquid raw material in which the drug is dissolved or suspended in a binder solution is granulated into core fine particles (bare particles) by using a spray drying fluidized bed granulation apparatus. The apparatus to be used has been used in the pharmaceutical industry to granulate granules for tableting in general and can be used also to manufacture drug particles in the conventional technology which are granulated by layering drug to core particles of crystalline cellulose or the like. Unlike in the conventional technology, however, since no fluidized bed of core particles is present, it is required that instead of this, initial fine particles are initially formed from the liquid raw material, the mixture of the drug and the binder is layered therearound, and the resultant is caused to grow into large particles. Therefore, as far as the liquid raw material is sprayed as mist from a nozzle toward the central portion of the apparatus, a position of the nozzle is arbitrary. However, a bottom spray method in which the nozzle is located in the central portion of the bottom of the apparatus and the mist is sprayed upward along the central axis of the apparatus is the most preferable.

Figure 1:
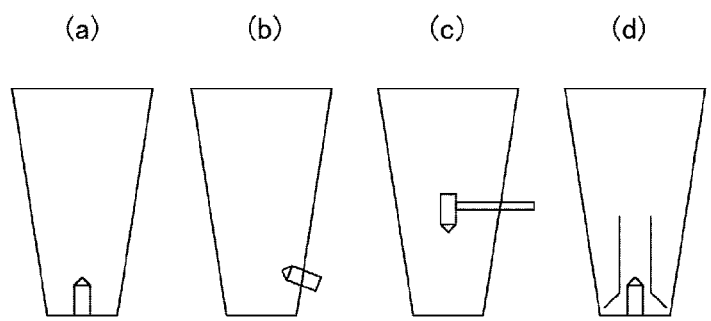
FIGS. 1(a)-(d) are schematic diagrams illustrating a method of spraying a liquid raw material to a spray drying fluidized bed granulation apparatus.

FIG. 1 is a schematic diagram illustrating a method of spraying the liquid to the spray drying fluidized bed granulation apparatus. In FIG. 1, a view (a) illustrates a bottom spray method with no inner cylinder; a view (b) illustrates a tilting spray method; a view (c) illustrates a top spray method; and a view (d) illustrates a bottom spray method with the inner cylinder being installed. The bottom spray method and in particular, the bottom spray method (a) with no inner cylinder is the most suitable for the present invention.

It is only required for a blending amount of the binder in the liquid raw material to be a amount which allows components of the drug and the like dissolved or suspended in the binder solution to integrally adhere to one another after the spraying and drying. The blending amount of 20% by weight or less with respect to a weight of the components of the drug and the like dissolved or suspended therein is sufficient, and the blending amount of 3 to 10% by weight is preferable.

It is preferable that a solvent for the liquid raw material, used upon producing the core fine particles, is water. However, it is allowable that an organic solvent such as an alcohol is used. It is only required for the binder to be any binder used for the ordinary pharmaceutical preparation, and for example, the binder may be hydroxypropyl-cellulose, hydroxypropyl methyl cellulose, a homopolymer or a copolymer of vinylpyrrolidone, polyvinyl alcohol, ethyl cellulose, or the like.

In a case where the core fine particles are produced by employing this method, the production starts from the generation of misty elementary fine particles which are generated by initially spraying droplets of the liquid raw material from a spray nozzle directly to an inside of the apparatus and solidifying the droplets; the production undergoes a time zone in which the layering of the droplets of the liquid raw material to the elementary fine particles, the generation of the fine particle cores prepared by the layering, the growing thereof, and the generation of new elementary fine particles are present in a mixed manner; and thereafter, finally, the layering is applied to the fine particle cores of a fluidized bed, thereby obtaining the core fine particles. In this case, the time zone in which the generation and growing of the fine particle cores and the generation of the new elementary fine particles are present in the mixed manner is long. Therefore, when with respect to the core fine particles produced by employing the method according to the present invention, particle diameters are measured on a volumetric basis, an average particle diameter is 400 μm or less, a particle diameter ratio ($D_{90}/D_{10}$) with respect to particle size distribution calculated on a volumetric basis is 1.65 or more, or a coefficient of variation in the particle diameters is 24% or more, and thus, the first characteristic in that the particle size distribution is broad is exhibited.

In addition, the core fine particles produced by this method are obtained basically by continuously spraying the liquid raw material in which the drug is suspended or dissolved in the solution having the binder dissolved therein directly into the fluidized bed, for example, by employing the bottom spray method; and mainly include the two components of the drug and the binder. Thus, the second characteristic in that the particles have elasticity and in that it is made possible to make a drug content high, which far exceeds 70% by weight, is exhibited.

Basically, the liquid raw material is obtained by suspending or dissolving the drug in the solution having the binder dissolved therein. In a case where the drug is operated by suspending, in order to grow core fine particles each having a smooth spherical surface state while the layering is being applied to the elementary fine particles, it is required for an average particle diameter of the drug to be 15 μm or less, and preferably, to be 10 μm or less. In addition, other than the drug and the binder, a material for the preparation of pharmaceuticals, such as a saccharide, a sugar alcohol, light anhydrous silicic acid, and a hydrous silicon dioxide, may be freely used as necessary by dissolving or suspending in the liquid raw material. In addition, upon spraying the liquid raw material to the fluidized bed, on the condition that variation in particle sizes of core fine particles to be produced falls in a range according to the present invention, a material for the preparation of pharmaceuticals, whose average particle diameter is 50 μm or less, also can be suspended in the fluidized bed.

Process 2: Coating of Core Fine Particles with a Functional Polymer

Functional spherical fine particles (functional drug-containing particles) according to the present invention can be obtained by coating the core fine particles produced in Process 1 with a functional polymer film by using an apparatus such as a tumbling fluidized bed coating apparatus. An average particle diameter of the functional spherical fine particles produced as mentioned above is 400 μm or less.

Upon coating the core fine particles with a release control film, an enteric film, or a bitter taste masking film, when smoothness in surfaces of the core fine particles is required, prior to the coating, surface states of the core fine particles may be freely made further smooth such that a solution in which a mixture of a drug substance and a binder or a mixture of a binder and a sweetening agent, and the like is dissolved or suspended in water is sprayed to the core fine particles by using the tumbling fluidized bed coating apparatus, thereby applying further layering and seal coating to the core fine particles.

With respect to the functional film such as the release control film, the enteric film, and the bitter taste masking film, by applying the coating of each of the release control film and the enteric film whose amount is equivalent to approximately 40% by weight of a weight of the core fine particles or by applying the coating of the bitter taste masking film whose amount is 5 to 40% by weight of the weight of the core fine particles, pharmaceutical functions as the functional fine particles can be achieved. A solvent used upon coating the functional film may be either water or an organic solvent.

In the core fine particles, a small amount of fine particle cores are inevitably present in a mixed manner. Upon applying the coating of the functional film, the fine particle cores suspend outside of the zone of a tumbling layer of the core fine particles to be actually sprayed with droplets in a coating tank of the tumbling fluidized bed coating apparatus, and even coating of the functional film cannot be applied. Therefore, it is desired to remove the small amount of the fine particle cores. In reality, the amount of these fine particle cores is small so as to be unlikely to exert any influence on an average particle diameter and particle size distribution of the core fine particles.

As a release control film agent, used is ethyl cellulose; a polyethylacrylate-methylmethacrylate-trimethylammonio-ethylmethacrylatechlorid copolymer powder; and an aqueous dispersion which contains, in the form of latex, ethyl cellulose, an ethyl acrylate-methyl methacrylate-trimethyl-ammoniumethyl chloride copolymer, and an ethyl acrylate-methyl methacrylate copolymer; or the like.

As an enteric film agent, there are a hydroxypropyl methyl cellulose phthalate; hydroxypropyl methyl cellulose acetate succinate; a methacrylic acid-methyl methacrylate copolymer; a methacrylic acid-ethyl methacrylate copolymer; a methacrylic acid-ethyl acrylate copolymer; or the like. Of course, each of these is dissolved by using an organic solvent such as methanol, ethanol, isopropanol, and dichloromethane to be used, and an aqueous dispersion which contains in the form of latex each of these water-insoluble polymers may be also freely used.

As a bitter taste masking film agent, each of the above-mentioned release control film agents and enteric film agents can be used, of course, and polyvinylacetal diethylamino acetate; a methyl methacrylate-butyl methacrylate-dimethylaminoethyl methacrylate copolymer, or the like can be used.

The functional spherical fine particles produced as described above are high-content functional fine particles. Therefore, an amount of the functional fine particles contained in one tablet can be reduced, and it is thereby easy to manufacture a tablet having a size which withstands practical use, thus providing merit.

Further, the average particle diameter of these functional spherical fine particles is 400 μm or less, and the particle diameter ratio ($D_{90}/D_{10}$) calculated on a volumetric basis with respect to the particle size distribution is 1.65 or more, or the coefficient of variation in the particle diameters is 24% or more. Thus, this broad particle size distribution and the elasticity thereof become distinguished merits for manufacturing tablets containing these functional spherical fine particles.

When tablets are manufactured through a drying method by using the functional spherical fine particles produced by the conventional method, it is required that an excipient, a disintegrant, a lubricant, and other commonly used additive are added thereto, and pressurizing compression is conducted, thereby manufacturing tablets or orally disintegrating tablets. The functional spherical fine particles according to the present invention, however, are characterized in that because the particle size distribution is not sharp and sizes of the particles are uneven, and the particles have elasticity, the functional spherical fine particles are excellent in the moldability, and thus, it is not required to add the excipient enhancing the moldability for manufacturing the tablets, and by adding only the disintegrant and the lubricant, the tablets or the orally disintegrating tablets can be manufactured.

Process 3: Manufacturing of an Orally Disintegrating Tablet

When tablets such as orally disintegrating tablets are manufactured, in the ordinary drying method, besides functional spherical fine particles, saccharides and sugar alcohols which are advantageous in terms of moldability and a disintegrating property are added, and in addition thereto, a disintegrant and a lubricant are added and blended, thereby conducting tableting. According to the present invention, since the functional spherical fine particles has the particle size distribution and the elasticity which is advantageous in the moldability, a content of the functional spherical fine particles in a tablet is set to 50% to 90% by weight, preferably, is set to 60% to 90% by weight, and most preferably, is set to 65% to 85% by weight, and as other components, a disintegrant and a small amount of a lubricant for the prevention of sticking are added and blended to be compressed, thereby allowing small-sized orally disintegrating tablets having a necessary hardness and disintegrating property. Of course, it is indisputable that as necessary, in order to make taste pleasant as appropriate, in consideration of small-sized tablets, pharmaceutical additives such as saccharides and sugar alcohols, taste masking agents, flavoring agents, and the like can be blended in a range in which the total amount of the additives for tableting does not exceed a weight of the functional spherical fine particles.

In addition, a solution in which a water-soluble binder, a saccharide or a sugar alcohol are dissolved in water is added to the functional spherical fine particles according to the present invention; the resultant is kneaded through a wet method, thereby preparing wet granules; the wet granules are solidified by molds so as to have fixed sizes; and thereafter, drying is conducted, thereby allowing tablets having a sufficient hardness to be produced. In this case, because said spherical fine particles are bonded through the bonding force of the water-soluble binder, the saccharide or the sugar alcohol, it is not necessarily required to add other additives for tableting. Therefore, truly small-sized tablets whose each amount of the functional spherical fine particles contained in one tablet exceeds 80% by weight can be obtained. In the conventional drying compression method, since a compression pressure of 7.5 kN/cm$^2$ or more is required for the solidification, it is needed to pay attention to the deformation of the fine particles upon the compression. In contrast to this, in this wet molding drying method, since the applied pressure of 2 kN/cm$^2$ or less is sufficient, the load exerted on the fine particles is small, thereby causing the deformation of the particles to hardly occur, and the functions of the functional spherical fine particles such as the sustained release property, the enteric property, and the bitter taste masking are not changed by the pressure applied upon the compression molding. Thus, the small-sized tablets having the targeted functions can be easily obtained, hence making this method extremely useful.

The tablets manufactured by employing the wet molding drying method are solidified with the water-soluble binder, the saccharide or the sugar alcohol serving as the binder. When these components are returned to water, the components easily disintegrate, thereby achieving a quick disintegrating property, and also at this point, it is advantageous.

Further, it has been found that since the functional fine particles according to the present invention are excellent in the moldability and have the properties which allow the easy solidification, when said functional spherical fine particles are coated with the saccharide which can be amorphous; the resultant is solidified into tablet shapes under the compression pressure of 7.5 kN/cm$^2$ or less by the drying method; and thereafter, the humidifying and drying are conducted, thus allowing the manufacturing of the tablets having the sufficient hardness which withstands the distribution in the market. In this case, with respect to the weight of the functional fine particles, approximately 10% by weight of the saccharide is blended thereto, and said spherical fine particles are bonded by the bonding force of the saccharide. Therefore, it is not required to add other additives for tableting, and the truly small-sized tablets whose each amount of the functional spherical fine particles contained in one tablet exceeds 80% by weight can be obtained. In a case of functional spherical fine particles, whose cores are crystalline cellulose or the like, manufactured by employing the method in the conventional technology, since the moldability thereof is inferior, even when the functional spherical fine particles are coated with the amorphous saccharide, after the functional spherical fine particles are subjected to the compression molding as they are, the functional spherical fine particles do not have a hardness which allows the functional spherical fine particles to be taken out from a tableting machine. In contrast to this, it has also been found that only by adding a small amount of the lubricant to the fine particles coated with the amorphous saccharide according to the present invention, the tablets having the strength which allows the tablets to be taken out from the tableting machine after the application of the low pressure of 7.5 kN/cm$^2$ or less can be manufactured, and therefore, by conducting the moisture absorption and subsequently the drying for the tablets, the enhancement of the bonding force which is attributed to recrystallization of the saccharide is developed, thereby allowing the tablets having the sufficient strength to be manufactured. In this case, there obtained are large merits in that only two components of the functional spherical fine particles and the amorphous saccharide are used and compressed into the tablet, and the resultant is subjected to the humidifying and drying, thereby allowing the orally disintegrating tablets having the sufficient strength to be manufactured; and in that since the pressure applied upon the molding into the tablets is the low pressure of 7.5 kN/cm$^2$ or less, and preferably, 5 kN/cm$^2$ or less, it is not needed to worry about the destruction of the sustained release property, the enteric property, and the bitter taste masking function of the functional spherical fine particles by the compression pressure. As the method of coating of the amorphous saccharide, preferable is a method in which the saccharide which is in a crystalline state allowing the saccharide to be amorphous is dissolved in a solvent, the functional fine particles are coated with this, and the drying is conducted. The added amount of the amorphous saccharide of 30% by weight or less, and preferably, of 20% or less with respect to the weight of the functional spherical fine particles is sufficient, and the amount of the functional spherical fine particles in a tablet exceeds 75% by weight, thereby achieving the miniaturization of the tablets.

In the tablets manufactured by employing the low-pressure molding humidifying drying method, the saccharide is the binder for tableting. The saccharide is quickly dissolved in water and develops the action as a disintegrant, thereby achieving the quick disintegrating property and allowing the orally disintegrating tablets to be easily obtained.

In manufacturing the tablets by employing this low-pressure molding humidifying drying method, the method for manufacturing the functional spherical fine particles which are excellent in the moldability has been found, and this method is the particularly characteristic tableting method which draws on the characteristics of said functional spherical fine particles in the highest manner and leads to the method for manufacturing the small-sized tablets.

The present invention disclosed above is particularly effective as the method in which the drug whose drug content is high is used to prepare the functional spherical fine particles; and the tablets or orally disintegrating tablets which have said functional spherical fine particles blended therein and are small-sized are manufactured by the drying method, the wet molding drying method, or the low-pressure molding humidifying drying method. Needless to say, also drug whose content is low is used to prepare functional spherical fine particles by employing the method equivalent to the present invention; and by using said fine particles, tablets or orally disintegrating tablets can be manufactured by employing the tableting method according to the present invention.

In the present invention, the orally disintegrating tablet means a tablet which disintegrates in the oral cavity within specifically, one minute, and preferably, 45 seconds. For the disintegration in the above-mentioned manner, it is required to add at least the disintegrant and the lubricant thereto and to conduct the compression molding. In the case where the functional spherical fine particles according to the present invention are used and the orally disintegrating tablets are manufactured through the pressurization compression by the drying method, only by adding the disintegrant whose amount is approximately 0.65 parts by weight or less with respect to the added amount of the functional spherical fine particles of 1 part by weight and a small amount of the lubricant for prevention of pestle sticking, the orally disintegrating tablets having the sufficient hardness and the targeted disintegrating property can be easily manufactured.

As the disintegrant, a starch, carmellose, carmellose calcium, croscarmellose sodium, crospovidone, low substituted hydroxy-propylcellulose, or the like is arbitrarily used alone or in combination of any thereof. In addition, a disintegrant having an effervescent tablet concept can also be used. In the case of the orally disintegrating tablets, since palatability, a disintegrating property, and taste are important, needless to say, a sweetening agent, a taste masking agent, or the like can be added thereto.

In the case where the functional spherical fine particles are subjected to the compression molding by the drying method, the tablets having the sufficient tablet strength and the favorable disintegrating property can be manufactured by employing the method in which only the disintegrant is added and the molding is conducted, as described above. Other than the disintegrant, however, it is arbitrary to add the vehicle such as the saccharide and the sugar alcohol as necessary and to conduct the tableting.

In the case of the drying method, at least one kind of a disintegrant and a lubricant may be added to the functional spherical fine particles, sugar or sugar alcohol and a sweetening agent or the like may be arbitrarily added thereto, and the tableting may be conducted. However, it is convenient to subject these additives which exclude the lubricant and include the functional fine particles or only these additives to granulation by using a bonding liquid such as an appropriately pregelatinized starch solution and conduct the drying, thereby preparing particles; to add the prepared particles; and to conduct the tableting.

In addition, by using the functional spherical fine particles according to the present invention, tables can be manufactured by employing the so-called wet molding drying method in which the water-soluble binder such as the vinylpyrrolidone homopolymer or copolymer, the hydroxypropyl-cellulose compound, the starch, and the polyvinyl alcohol and the solution in which the saccharide such as sucralose, maltose, fructose, maltitol, xylitol, sorbitol, and lactitol or the sugar alcohol is dissolved in water are added to said fine particles; the resultant is kneaded by the wet method, thereby preparing the wet granules; the prepared wet granules are solidified by the molds so as to have fixed sizes; and thereafter, the drying is conducted. As the drying method, in general, air drying at a temperature of 30° C. to 60° C. is adopted.

Furthermore, by using the functional spherical fine particles according to the present invention, tables can be manufactured by employing the so-called low-pressure molding humidifying drying method in which the saccharide such as maltose, sorbitol, trehalose, lactitol, fructose, and glucose which is in the crystalline state allowing the saccharide to be amorphous is dissolved in the solvent; this is sprayed to the functional fine particles, thereby applying the coating; the drying is conducted; a small amount of the lubricant such as magnesium stearate is added to the prepared particles; the resultant is subjected to the compression pressure at 5 kN/cm$^2$ or less to compress into tablets; and the tablets are subjected to the humidification; and thereafter, the tablets are subjected to the drying. This is a method in which the saccharide in the amorphous state is converted to the saccharide in a crystalline state, thereby making the system stable, and as a result, the strength of the tablets is enhanced, thereby obtaining the tablets having the sufficient strength which withstands the distribution in the market. The humidification conditions is 40 to 100 RH % under the condition of a temperature at 20° C. to 50° C. and preferably, is 50 to 90 RH % under the condition of a temperature at 20° C. to 40° C. As the drying condition, preferably, air drying at 30° C. to 60° C. is adopted.

In the case of the tablets manufactured by employing the wet molding drying method and the low-pressure molding humidifying drying method, said spherical fine particles are bonded by the bonding force of the water-soluble binder, the saccharide, and the sugar alcohol, and when returned to water, these exert their action as the disintegrant. Therefore it is not necessarily required to add other additives for tableting, and the truly small-sized tablets whose each amount of the functional spherical fine particles contained in one tablet exceeds 80% by weight can be obtained. Of course, in order to make the palatability in the oral cavity pleasant, needless to say, the sweetening agent, the taste masking agent, and the like can be blended, and it is also arbitrary to blend other additives for tableting as necessary.

In the case of the tablets manufactured by employing the wet molding drying method and the low-pressure molding humidifying drying method, in consideration of the enhancement of the strength and the quick disintegrating property of the tablets, for example, it is arbitrary to mix and use the saccharide and the water-soluble binder or the saccharide and the sugar alcohol. As the blended mount of the saccharide, the sugar alcohol, and the water-soluble binder, 25% by weight or less or preferably, 20% by weight or less with respect to the weight of the functional spherical fine particles is sufficient, thereby achieving the miniaturization.

EXAMPLES

Hereinafter, by using examples which do not intend any limitation, the present invention will be illustrated. In the examples, "part/parts" and "%" are on a weight basis unless otherwise specified.

Example 1

A liquid raw material was prepared by suspending 165 g of ambroxol hydrochloride (average particle diameter: approximately 3 μm) in a solution in which 19.8 g of hydroxypropyl-cellulose (trade name: HPC-L, Nippon Soda Co., Ltd.) was dissolved in 640.2 g of purified water; the prepared liquid raw material was continuously sprayed into a spray drying fluidized bed granulating machine (MP-01-SPC model with no inner cylinder, Powrex Corporation) under the conditions of an inlet air temperature at 90° C. and an inlet air flow rate of 40 to 60 m$^3$/h from a nozzle having an orifice diameter of 1.2 mm, thereby conducting layering; drying was conducted; and thereafter, particles each having a particle diameter of 105 μm or less were removed, thereby obtaining core fine particles. The above-described operation was conducted twice, the obtained particles were mixed, and thereafter, the obtained particles were used in the below-described experiments. A layering solution was prepared by suspending 40 g of the ambroxol hydrochloride (average particle diameter: approximately 3 μm) in a solution in which 9.8 g of the hydroxypropyl-cellulose (trade name: HPC-L) was dissolved in 338.4 g of the purified water. A seal coating solution was prepared by dissolving 5.25 g of hydroxypropyl methyl cellulose (trade name: TC-5E, Shin-Etsu Chemical Co., Ltd.) and 2.25 g of sucralose (trade name: Sucralose P, San-Ei Gen F.F.I., Inc.) in 142.5 g of the purified water. A release control film solution was prepared by dissolving 85.71 g of ethyl cellulose (trade name: ETHO-CEL 10, Dow) and 26.79 g of hydroxypropyl methyl cellulose (trade name: TC-5R, Shin-Etsu Chemical Co., Ltd.) in 1293.75 g of an 80-% by weight ethanol solution (mixed liquid of ethanol 8: purified water 2). The core fine particles whose amount was 250 g were inputted into the tumbling fluidized bed coating granulating machine (Powrex Corporation: MP-01 model), and while being caused to be flowing, the layering solution was sprayed thereto, thereby preparing layering fine particles. Subsequently, the layering fine particles whose amount was 250 g were inputted into the tumbling fluidized bed granulating machine (Powrex Corporation: MP-01 model), the seal coating solution was sprayed thereto for coating, thereby preparing seal coating fine particles. Thereafter, subsequently, the release control film solution was sprayed thereto for coating, thereby obtaining spherical fine particles having a sustained release property (these fine particles are referred to as "Example 1 particles"). An average particle diameter of these spherical fine particles having the sustained release property calculated on a volumetric basis was 247.7 μm, and a particle diameter ratio ($D_{90}/D_{10}$) thereof with respect to particle size distribution was 1.83. In addition, an arithmetic standard deviation of the particle diameters was 69.6 μm, and a coefficient of variation in the particle diameters was 28.1%. In Example 1, the contents of the ambroxol hydrochloride in the core fine particles and the spherical fine particles having the sustained release property were 87.8 wt % and 59.3 wt %, respectively.

Example 2

A liquid raw material was prepared by suspending 397 g of ambroxol hydrochloride (average particle diameter: approximately 3 μm) in a solution in which 47.68 g of hydroxypropyl-cellulose (trade name: HPC-L, Nippon Soda Co., Ltd.) was dissolved in 1543 g of purified water; the prepared liquid raw material was continuously sprayed into a spray drying fluidized bed granulating machine (MP-01-SPC model with no inner cylinder) under the conditions of an inlet air temperature at 90° C. and an inlet air flow rate of 40 to 60 m³/h from a nozzle having an orifice diameter of 1.2 mm, thereby conducting layering; drying was conducted; and thereafter, particles each having a particle diameter of 105 μm or less were removed, thereby obtaining core fine particles. A layering solution was prepared by suspending 20 g of the ambroxol hydrochloride (average particle diameter: approximately 3 μm) in a solution in which 4.9 g of the hydroxypropyl-cellulose (trade name: HPC-L) was dissolved in 169.2 g of the purified water. A seal coating solution was prepared by dissolving 5.25 g of hydroxypropyl methyl cellulose (trade name: TC-5E, Shin-Etsu Chemical Co., Ltd.) and 2.25 g of sucralose in 142.5 g of the purified water. A release control film solution was prepared by dissolving 85.71 g of ethyl cellulose (trade name: ETHOCEL 10) and 26.79 g of TC-5R in 1293.75 g of an 80-% by weight ethanol solution. The core fine particles whose amount was 250 g were inputted into the tumbling fluidized bed granulating machine (MP-01 model), and while being caused to be flowing, the layering solution was sprayed thereto, thereby preparing layering fine particles. Subsequently, the layering fine particles whose amount was 250 g were inputted into the above-mentioned machine, the seal coating solution was sprayed thereto for coating, thereby preparing seal coating fine particles. Thereafter, subsequently, the release control film solution was sprayed thereto for coating, thereby obtaining spherical fine particles having a sustained release property (these fine particles are referred to as "Example 2 particles"). An average particle diameter of these spherical fine particles having the sustained release property calculated on a volumetric basis was 386.5 μm, and a particle diameter ratio ($D_{90}/D_{10}$) thereof with respect to particle size distribution was 1.84. In addition, an arithmetic standard deviation of the particle diameters was 108.7 μm, and a coefficient of variation in the particle diameters was 28.1%. In Example 2, the contents of the ambroxol hydrochloride in the core fine particles and the spherical fine particles having the sustained release property were 88.5 wt % and 59.8 wt %, respectively.

Comparative Example 1

A layering liquid was prepared by dispersing, through stirring, 254.8 g of ambroxol hydrochloride (average particle diameter: approximately 3 μm) in a solution in which 62.4 g of HPC-L was dissolved in 2156 g of purified water. A seal coating liquid was prepared by adding 5.25 g of hypromellose (trade name: TC-5E, Shin-Etsu Chemical Co., Ltd.) and 2.25 g of sucralose (trade name: Sucralose P, San-Ei Gen F.F.I., Inc.) to 142.5 g of purified water, which were stirred and dispersed therein. A release control solution was prepared by adding 1293.75 g of an 80-% by weight ethanol solution to 85.71 g of ethyl cellulose (trade name: ETHOCEL 10, Dow) and 26.79 g of hypromellose (trade name: TC-5R, Shin-Etsu Chemical Co., Ltd.) which were stirred and dissolved therein. Inputted into a tumbling fluidized bed coating granulating machine (MP-01 model) was 250 g of crystalline cellulose (granules) (trade name: CELPHERE CP102, Asahi Kasei Chemicals Corporation), and while being caused to be tumbling and flowing, the layering liquid was sprayed thereto, thereby conducting layering. After the spraying, drying was conducted and thereafter, particles each having a particle diameter of 105 μm or less were removed, thereby obtaining drug layering fine particles. Subsequently, seal coating fine particles were prepared by inputting 250 g of the layering fine particles into the above-mentioned machine and spraying the seal coating solution thereto, and thereafter, subsequently, spraying the release control solution thereto for coating, thereby obtaining spherical fine particles having a sustained release property (these fine particles are referred to as "Comparative Example 1 particles"). An average particle diameter of these spherical fine particles having the sustained release property calculated on a volumetric basis was 283.6 μm, and a particle diameter ratio ($D_{90}/D_{10}$) thereof with respect to particle size distribution was 1.63. In addition, an arithmetic standard deviation of the particle diameters was 60.2 μm, and a coefficient of variation in the particle diameters was 21.2%. In Comparative Example 1, the contents of the ambroxol hydrochloride in the core fine particles and the spherical fine particles having the sustained release property were 44.9 wt % and 30.4 wt %, respectively.

Reference Example 1

Manufacturing of Disintegrant Granule

A corn starch solution was prepared by suspending 150 g of corn starch and 7.5 g of acesulfame potassium (trade name: Sunett, Kyowa Kirin Foods Co., Ltd.) in 850 g of purified water, heating the resultant at a temperature of 58° C. while being stirred, and thereafter, conducting cooling. Inputted to a tumbling fluidized bed coating granulating machine (MP-01 model) were 513 g of D-mannitol (trade name: PEARLITOL 50C, Roquette Japan), 150 g of crystalline cellulose (trade name: CEOLUS KG-802, Asahi Kasei Chemicals Corporation), 45 g of carmellose (trade name:NS-300, GOTOKU CHEMICAL COMPANY LTD.), and 22.5 g of crospovidone (trade name: Kollidon CL-SF, BASF), while being caused to be flowing, the corn starch solution was sprayed thereto, and granulating and drying were conducted. The particles obtained as above are referred to as "Reference Example 1 granule").

Reference Example 2

Manufacturing of Disintegrant-Mixed Granule

Weighed were 1000 g of mannitol for direct compression (trade name: Granutol R, Freund Corporation), 480 g of carmellose (trade name: NS300, GOTOKU CHEMICAL COMPANY LTD.), 280 g of precipitated calcium carbonate (Bihoku Funka Kogyo Co., Ltd.), 80 g of light anhydrous silicic acid (trade name: Adsolider 101, Freund Corporation), and 160 g of crystalline cellulose (trade name: KG-802, Asahi Kasei Chemicals Corporation), and the weighed materials were inputted to a V-type rotary powder mixer (YT-2 V model, Takizawa Medical Industry Co., Ltd.) and were mixed. This is referred to as "Reference Example 2 granule".

Example 3

As a material of spherical fine particles having a sustained release property, Example 1 particles or Example 2 particles were used; as additives, Reference Example 1 granule, Reference Example 2 granule, a corn starch granulated material (trade name: Graflow M, NIPPON STARCH CHEMICAL CO., LTD.), NS-300, or Kollidon CL-SF and sodium stearyl fumarate (trade name: PRUV, JRS Pharma) were used; the components were weighed as shown in Table 1 and mixed; and the weighed and mixed components were compressed by using a pestle having a diameter of 10 mm under a tableting pressure of 10 kN into tablets having a weight of 340 mg. With respect to the obtained tablets, a hardness and an intraoral disintegrating time were measured. As a result, it was found that even when with respect to 100 parts of the spherical fine particles, the blending amount of the disintegrant was far below 100 parts, the hardness was 40 N or more withstanding the distribution in the market and that it was made possible to manufacture the tablets whose intraoral disintegrating time was within 30 seconds.

TABLE 1

Hardness and Intraoral Disintegrating Time of Tablet

| | | | | | | | | | | |
|---|---|---|---|---|---|---|---|---|---|---|
| Example 1 particle | 60.0 | 75.0 | 60.0 | 75.0 | 75.0 | | | | | |
| Example 2 particles | | | | | | 60.0 | 75.0 | 60.0 | 75.0 | 75.0 |
| Reference Example 1 particles | 39.5 | 24.5 | | | | 39.5 | 24.5 | | | |
| Reference Example 2 particles | | | 39.5 | | | | | 39.5 | | |
| Graflow | | | | 18.0 | | | | | 18.0 | |
| NS300 | | | | | 18.0 | | | | | 18.0 |
| Kollidon | | | | 6.5 | 6.5 | | | | 6.5 | 6.5 |
| PRUV | 0.5 | 0.5 | 0.5 | 0.5 | 0.5 | 0.5 | 0.5 | 0.5 | 0.5 | 0.5 |
| Tablet hardness | 70.7 | 52.5 | 51.5 | 62.5 | 52.3 | 66.3 | 50.6 | 49.7 | 60.2 | 49.1 |
| Disintegrating time | 15 | 22 | 15 | 25 | 15 | 15 | 18 | 14 | 20 | 16 |

A blending amount of each component is based on wt. part; a tablet hardness on N; and an intraoral disintegrating time on seconds.

Comparative Example 2

As a material of spherical fine particles having a sustained release property, Comparative Example 1 particles were used; the components were weighed as shown in Table 2 and mixed; and the weighed mixed components were compressed by using a pestle having a diameter of 10 mm under a tableting pressure of 10 kN into tablets having a weight of 340 mg. With respect to the obtained tablets, a hardness and an intraoral disintegrating time were measured. As a result, when with respect to 100 parts of the spherical fine particles, the blending amount of the disintegrant was below 100 parts, it was impossible to manufacture the tablets having a hardness which was able to sufficiently withstand the distribution in the market, the hardness withstanding the distribution therein being 40 N or more. In addition, in order to obtain the sufficient hardness, the blending amount of Comparative Example 1 particles in the tablet was required to be 50% by weight or less.

TABLE 2

Hardness and Intraoral Disintegrating Time of Tablet

| | | | | | | |
|---|---|---|---|---|---|---|
| Comparative Example 1 particles | 60.0 | 75.0 | 60.0 | 75.0 | 75.0 | 42.0 |
| Reference Example 1 particles | 39.5 | 24.5 | | | | 57.5 |
| Reference Example 1 particles | | | 39.5 | | | |
| Graflow | | | | 18.0 | | |
| NS300 | | | | | 18.0 | |
| Kollidon | | | | 6.5 | 6.5 | |
| PRUV | 0.5 | 0.5 | 0.5 | 0.5 | 0.5 | 0.5 |
| Tablet hardness (unit: N) | 22.3 | 13.5 | 21.3 | 20.1 | 25.4 | 49.0 |
| Disintegrating time (unit: seoond) | 12 | 18 | 14 | 16 | 10 | 15 |

A blending amount of each component is based on wt. part.

Example 4

A liquid raw material was prepared by dissolving or suspending 300 g of valacyclovir hydrochloride in a solution in which 16.67 g of hydroxypropyl-cellulose (trade name: HPC-M, Nippon Soda Co., Ltd.) was dissolved in 1350 g of water; the prepared liquid raw material was continuously sprayed into a spray drying fluidized bed granulating machine (MP-01-SPC model with no inner cylinder) under the conditions of an inlet air temperature at 90° C. and an inlet air flow rate of 40 to 60 m³/h from a nozzle having an orifice diameter of 1.2 mm, thereby conducting layering; drying was conducted; and thereafter, particles each having a particle diameter of 105 μm or less were removed, thereby obtaining core fine particles. A bitter taste masking solution was prepared by dissolving 54 g of ethyl cellulose (trade name: ETHOCEL 7, Dow) and 13.5 g of hypromellose (trade name: TC-5R) in 776.25 g of an 80-% by weight ethanol solution. The core fine particles whose amount was 250 g were inputted into a tumbling fluidized bed coating granulating machine (MP-01 model), and while being caused to be tumbling and flowing, the bitter taste masking solution was sprayed thereto, thereby conducting layering. An average particle diameter of these bitter taste masking spherical fine particles calculated on a volumetric basis was 233.4 μm, and a particle diameter ratio ($D_{90}/D_{10}$) thereof with respect to particle size distribution was 1.98. In addition, an arithmetic standard deviation of the particle diameters was 75.4 μm, and a coefficient of variation in the particle diameters was 32.3%. In Example 4, the contents of the valacyclovir hydrochloride in the core fine particles and the bitter taste masking spherical fine particles were 94.7 wt % and 74.6 wt %, respectively.

Next, the prepared bitter taste masking spherical fine particles were used; the components were weighed as shown in Table 3 and mixed; and the weighed and mixed components were compressed by using a pestle having a diameter of 10 mm under a tableting pressure of 10 kN into tablets having a weight of 340 mg. With respect to the obtained tablets, a hardness and an intraoral disintegrating time were measured. As a result, it was found that even when with respect to 100 parts of the spherical fine particles, the blending amount of the disintegrant was far below 100 parts, the hardness was a hardness of 40 N or more withstanding the distribution in the market and that it was made possible to manufacture the tablets whose intraoral disintegrating time was within 30 seconds.

TABLE 3

Hardness and Intraoral Disintegrating Time of Tablet

| | | | |
|---|---|---|---|
| Bitter taste masking spherical fine particles | 75.0 | 75.0 | 75.0 |
| NS-300 | 18.0 | | |
| CEOLUS KG-802 | | 12.25 | |
| Graflow M | | 12.25 | 18.0 |
| Kollidon CL-SF | 6.5 | | 6.5 |
| PRUV | 0.5 | 0.5 | 0.5 |
| Tablet hardness (unit: N) | 56.5 | 45.8 | 60.0 |
| Disintegrating time (unit: second) | 12 | 10 | 26 |

A blending amount of each component is based on wt. part.

Example 5

A liquid raw material was prepared by dissolving or suspending 300 g of a diltiazem hydrochloride in a solution in which 33.33 g of hydroxypropyl-cellulose (trade name: HPC-L) was dissolved in 777.77 g of water; the prepared liquid raw material was continuously sprayed into a spray drying fluidized bed granulating machine (MP-01-SPC model with no inner cylinder) under the conditions of an inlet air temperature at 90° C. and an inlet air flow rate of 40 to 60 m³/h from a nozzle having an orifice diameter of 1.2 mm, thereby conducting layering; drying was conducted; and thereafter, particles each having a particle diameter of 105 μm or less were removed, thereby obtaining core fine particles. A release control solution was prepared by suspending talc (Matsumurasangyo) in a solution in which 6.11 g of methylethyl acrylatemethacrylate methacrylic acid trimethylammonium ethyl chloride copolymer (EUDRAGIT RL100, Evonik Industries), 54.99 g of polyethylacrylate-methylmethacrylate-trimethylammonioethylmethacrylatechlorid copolymer (EUDRAGIT RS100, Evonik Industries), and 6.11 g of triethyl citrate (Citroflex 2, MORIMURA BROS., INC.) were dissolve in 1124.24 g of an 80-% by weight ethanol solution. The core fine particles whose amount was 250 g were inputted into a tumbling fluidized bed coating granulating machine (MP-01 model), and while being caused to be tumbling and flowing, the release control solution was sprayed thereto, thereby conducting layering. An average particle diameter of these release control spherical fine particles calculated on a volumetric basis was 250.1 μm, and a particle diameter ratio ($D_{90}/D_{10}$) thereof with respect to particle size distribution was 2.07. In addition, an arithmetic standard deviation of the particle diameters was 80.9 μm, and a coefficient of variation in the particle diameters was 32.3%. In Example 5, the contents of the diltiazem hydrochloride in the core fine particles and the release control spherical fine particles were 90.0 wt % and 70.9 wt %, respectively.

Next, the prepared release control spherical fine particles were used; the components were weighed as shown in Table 4 and mixed; and the weighed and mixed components were compressed by using a pestle having a diameter of 10 mm under a tableting pressure of 10 kN into tablets having a weight of 340 mg. With respect to the obtained tablets, a hardness and an intraoral disintegrating time were measured. As a result, it was found that even when with respect to 100 parts of the spherical fine particles, the blending amount of the disintegrant was far below 100 parts, the hardness was 40 N or more withstanding the distribution in the market and that it was made possible to manufacture the tablets whose intraoral disintegrating time was within 30 seconds.

TABLE 4

Hardness and Intraoral Disintegrating Time of Tablet

| | | | | |
|---|---|---|---|---|
| Release control spherical fine particles | 75.0 | 75.0 | 75.0 | 75.0 |
| Reference Example 2 powder | 24.5 | | | |
| NS-300 | | 24.5 | 12.25 | |
| CEOLUS KG-802 | | | 12.25 | |
| Graflow M | | | | 18.0 |
| Kollidon CL-SF | | | | 6.5 |
| PRUV | 0.5 | 0.5 | 0.5 | 0.5 |
| Tablet hardness (unit: N) | 36.5 | 45.8 | 60.0 | 79.0 |
| Disintegrating time (unit: second) | 20 | 10 | 13 | 29 |

Comparative Example 3

A sub-coating solution was prepared by suspending 6 g of talc in a solution in which 12 g of TC-5R and 2 g of Polysorbate 80 (trade name: Tween 80, Nikko Chemicals Co., Ltd.) were weighed and dissolved in 336 g of purified water. A layering solution was prepared by weighing and dissolving or dispersing 330.6 g of pioglitazone hydrochloride, 200 g of TC-5R, 160 g of Glycine (Yuki Gosei Kogyo Co., Ltd.), and 10 g of Tween 80 in 4775 g of an 80-% by weight ethanol solution.

A bitter taste masking solution was prepared by weighing and dissolving or dispersing 151 g of aminoalkyl methacrylate copolymer E (EUDRAGIT E100, Evonik Industries), 5 g of ethyl cellulose (trade name: ETHOCEL 7, Dow), 19 g of light magnesium carbonate (Kyowa Chemical Industry Co., Ltd.), 2.5 g of sodium stearate (trade name: PRUV, Rettenmaier Japan Co., Ltd.), 5 g of sucralose (San-Ei Gen F.F.I., Inc.), 40.5 g of hydrous silicon dioxide (trade name:

Carplex, DSL. Japan), and 17 g of talc (Matsumurasangyo) in a mixed liquid of 1263.5 g of ethanol and 140.5 g of purified water.

Inputted into a tumbling fluidized bed granulating coating machine (SFC-MINI, Freund Corporation) was 479.4 g of CELPHERE CP102; while being caused to be tumbling and flowing, the above-mentioned sub-coating solution was sprayed thereto; and thereafter, the layering liquid was sprayed, thereby conducting layering. After the spaying and then the drying, particles each having a particle diameter of 105 μm or less were removed, thereby obtaining drug layering fine particles. Subsequently, 600 g of the core fine particles were inputted into the above-mentioned machine, and the bitter taste masking solution was sprayed thereto, thereby obtaining bitter taste masking spherical fine particles. An average particle diameter of these spherical fine particles calculated on a volumetric basis was 265 μm, and a particle diameter ratio ($D_{90}/D_{10}$) thereof with respect to particle size distribution was 1.63. In addition, an arithmetic standard deviation of the particle diameters was 59.1 μm, and a coefficient of variation in the particle diameters was 22.3%. In Comparative Example 3, the contents of the pioglitazone hydrochloride in the drug layering fine particles and the bitter taste masking spherical fine particles were 27.6 wt % and 19.4 wt %, respectively.

Next, the prepared bitter taste masking spherical fine particles were used, the components were weighed as shown in Table 5 and mixed; and the weighed and mixed components were compressed by using a pestle having a diameter of 10 mm under a tableting pressure of 10 kN into tablets having a weight of 340 mg. With respect to the obtained tablets, a hardness and an intraoral disintegrating time were measured. As a result, when with respect to 100 parts of the spherical fine particles, the blending amount of the disintegrant was below 100 parts, it was impossible to manufacture the tablets having a hardness which was able to sufficiently withstand the distribution in the market, the hardness withstanding the distribution therein being 40 N or more. In addition, in order to obtain the sufficient hardness, the blending amount of Comparative Example 1 particles in the tablet was required to be 50% by weight or less.

TABLE 5

Hardness and Intraoral Disintegrating Time of Tablet

| | | | | | | |
|---|---|---|---|---|---|---|
| Bitter taste masking spherical fine particles | 60.0 | 75.0 | 60.0 | 75.0 | 75.0 | 47.3 |
| Reference Example 1 particles | 39.5 | 24.5 | | | | |
| Reference Example 2 powder | | | 39.5 | | | |
| Granutol R | | | | | | 37.5 |
| Graflow M | | | | 18.0 | | |
| NS-300 | | | | | 18.0 | |
| Kollidon CL-SF | | | | 6.5 | 6.5 | 3.8 |
| LH-11 | | | | | | 6.7 |
| CEOLUS KG-802 | | | | | | 4.2 |
| PRUV | 0.5 | 0.5 | 0.5 | 0.5 | 0.5 | 0.5 |
| Tablet hardness (unit: N) | 29.3 | 19.7 | 30.3 | 25.1 | 30.4 | 55.1 |
| Disintegrating time (unit: second) | 15 | 16 | 14 | 19 | 16 | 20 |

A blending amount of each component is based on wt. part. A material LH-11 is low substituted hydroxypropylcellulose manufactured by Shin-Etsu Chemical Co., Ltd.

Example 6

Figure 2:
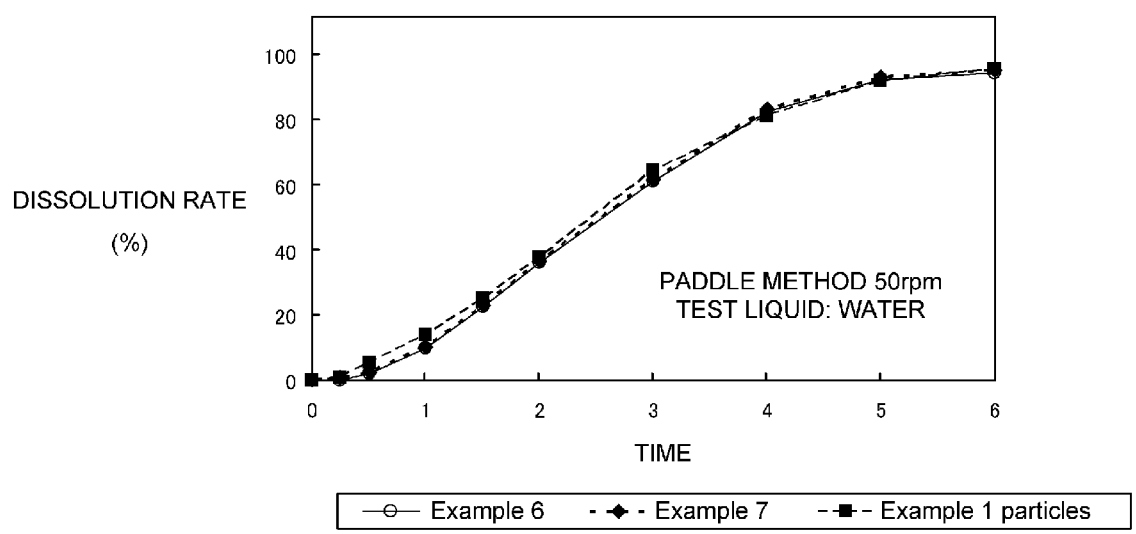
FIG. 2 is a graph showing dissolution profiles of a tablet in Example 6 and a tablet in Example 7.

Wet lump granules were prepared by using Example 1 particles; dropping 1.83 parts by weight (1.4 parts by weight as a solid content) of maltose starch syrup (trade name: MALSTAR, Hayashibara Co., Ltd.) to 7.5 parts by weight of Example 1 particles; kneading the resultant; and mixing the maltose starch syrup thoroughly and evenly in the drug containing fine particles. The obtained wet lump granules were molded by using a circular mold having a diameter of 15 mm under a pressure of 1 kN through compression filling; after taking out the resultant, the resultant was subjected to vacuum drying at a temperature of 40° C. for 12 hours, thereby producing orally disintegrating tablets (600 mg in mass). A hardness of this tablet was 60 N and an intraoral disintegrating time was within 15 seconds. In addition, dissolution profiles of this tablet and Example 1 particles were the same as each other as shown in FIG. 2, and it was considered that the breakage of the film with which the particles were coated upon tableting did not occur.

Example 7

Wet lump granules were prepared by using Example 1 particles; dropping 1 part by weight (0.3 part by weight as a solid content) of a 30% aqueous solution of polyvinylpyrrolidone (trade name: Plasdone K-30, ISP Japan) to 5.5 parts by weight of Example 1 particles; kneading the resultant; and mixing a binder thoroughly and evenly in the drug containing fine particles. The obtained wet lump granules were molded by using a circular mold having a diameter of 15 mm under a pressure of 1 kN through compression filling; after taking out the resultant, the resultant was subjected to vacuum drying at a temperature of 40° C. for 12 hours, thereby producing orally disintegrating tablets (600 mg in mass). A hardness of this tablet was 70 N and an intraoral disintegrating time was within 15 seconds. In addition, dissolution profiles of this tablet and Example 1 particles were the same as each other as shown in FIG. 2, and it was considered that the breakage of the film with which the particles were coated upon tableting did not occur.

Example 8

Wet lump granules were prepared by using the bitter taste masking spherical fine particles prepared in Example 4; dropping 1.83 parts by weight (1.4 parts by weight as a solid content) of MALSTAR to 7.5 parts by weight of the bitter taste masking spherical fine particles; kneading the resultant; and mixing glutinous starch syrup thoroughly and evenly in the drug containing fine particles. The obtained wet lump granules were molded by using a circular mold having a diameter of 15 mm under a pressure of 1 kN through compression filling; after taking out the resultant, the resultant was subjected to vacuum drying at a temperature of 40° C. for 12 hours, thereby producing orally disintegrating tablets (600 mg in mass). A hardness of this tablet was 65 N and an intraoral disintegrating time was within 15 seconds.

Example 9

Wet lump granules were prepared by using the bitter taste masking spherical fine particles prepared in Example 4; dropping 1 part by weight (0.3 part by weight as a solid content) of a 30% aqueous solution of Plasdone K-30 to 5.5 parts by weight of the bitter taste masking spherical fine particles; kneading the resultant; and mixing a binder thoroughly and evenly in the drug containing fine particles. The obtained wet lump granules were molded by using a circular mold having a diameter of 15 mm under a pressure of 1 kN through compression filling; after taking out the resultant, the resultant was subjected to vacuum drying at a temperature of 40° C. for 12 hours, thereby producing orally disintegrating tablets (600 mg in mass). A hardness of this tablet was 69 N and an intraoral disintegrating time was within 15 seconds.

Example 10

A liquid raw material was prepared by suspending 165 g of ambroxol hydrochloride (average particle diameter: approximately 3 μm) in a solution in which 19.8 g of hydroxypropyl-cellulose (trade name: HPC-L, Nippon Soda Co., Ltd.) was dissolved in 640.2 g of purified water; the prepared liquid raw material was continuously sprayed into a spray drying fluidized bed granulating machine (MP-01-SPC model with no inner cylinder, Powrex Corporation) under the conditions of an inlet air temperature at 90° C. and an inlet air flow rate of 40 to 60 m³/h from a nozzle having an orifice diameter of 1.2 mm, thereby conducting layering; drying was conducted; and thereafter, particles each having a particle diameter of 105 μm or less were removed, thereby obtaining core fine particles. The above-described operation was conducted twice, the obtained particles were mixed, and the obtained particles were used in the below-described experiments. A layering solution was prepared by suspending 40 g of the ambroxol hydrochloride (average particle diameter: approximately 3 μm) in a solution in which 9.8 g of the hydroxypropyl-cellulose (trade name: HPC-L) was dissolved in 338.4 g of the purified water. A release control solution was prepared by weighing 112.75 g of EUDRAGIT NE30D (an aqueous suspension whose solid content was 30%, Evonik Industries), 38.825 g of talc (Matsumurasangyo), and 7.35 g of HPC-L and dissolving or suspending the weighed components in 158.73 g of purified water. Layering fine particles were prepared by inputting 250 g of the core fine particles into a tumbling fluidized bed granulating machine (MP-01 model), and while being caused to be flowing, spraying the layering solution thereto. Subsequently, 250 g of the layering fine particles were inputted into the above-mentioned machine, and the release control film solution was sprayed thereto for coating, thereby obtaining release control spherical fine particles. An average particle diameter of these release control spherical fine particles was 238.0 μm, and a particle diameter ratio ($D_{90}/D_{10}$) thereof with respect to particle size distribution was 1.90. In addition, an arithmetic standard deviation of the particle diameters was 74.6 μm, and a coefficient of variation in the particle diameters was 31.3%. In Example 10, the contents of the ambroxol hydrochloride in the core fine particles and the spherical fine particles were 87.8 wt % and 53.7 wt %, respectively.

Inputted into the tumbling fluidized bed granulating machine (MP-01 model) were 250 g of the release control spherical fine particles; a solution in which 28.125 g of maltose (trade name: SUNMALT-GREEN, Hayashibara Co., Ltd.) and 3.125 g of polyvinyl-pyrrolidone (trade name: Plasdone K-30, ISP Japan) were dissolved in 125 g of purified water was sprayed thereto; granulation was conducted such that surfaces of the fine particles were coated with the maltose and the polyvinyl-pyrrolidone; and drying was conducted. Tableting was conducted by mixing 0.3 part of PRUV (sodium stearyl fumarate) to 100 pars of the particles prepared as described above; using a desktop tableting machine (HANDTAB-200, ICHIHASHI SEIKI); using a capsule-shaped pestle having a long diameter of 18.6 mm and a short diameter of 7.3 mm, and setting a tableting pressure at 2.5 kN, thereby obtaining tablets whose mass per tablet was 900 mg and initial hardness was 34 N. These tablets were preserved for 3 hours in warmed and humidified conditions at 25° C. and 75% RH by using a thermostatic and humidistatic machine (LH21-11M, NAGANO SCIENCE CO. LTD.) and thereafter, were dried by using a drying machine (PV-221, TABAI ESPEC CORP.) for 1 hour at 50° C. As a result, tablets whose hardness was 90 N and intraoral disintegrating time was within 30 seconds were obtained.

Example 11

A liquid raw material was prepared by dissolving or suspending 300 g of valacyclovir hydrochloride in a solution in which 16.67 g of hydroxypropyl-cellulose (trade name: HPC-M, Nippon Soda Co., Ltd.), 1.35 g of sucralose (trade name: Sucralose P, San-Ei Gen F.F.I. Inc.), 0.16 g of thaumatin (trade name: Sunsweet T, San-Ei Gen F.F.I., Inc.), and 5.40 g of sodium chloride (Naruto Salt Mfg. Co., Ltd.) were dissolved in 1350 g of purified water; the prepared liquid raw material was continuously sprayed into a spray drying fluidized bed granulating machine (MP-01-SPC model with no inner cylinder, Powrex Corporation) under the conditions of an inlet air temperature at 80° C. and an inlet air flow rate of 40 to 60 m³/h from a nozzle having an orifice diameter of 1.2 mm, thereby conducting layering; drying was conducted; and thereafter, particles each having a particle diameter of 425 μm or more and 105 μm or less were removed, thereby obtaining core fine particles. An undercoating solution was prepared by dissolving 9.65 g of ethyl cellulose (trade name: ETHOCEL 45, Dow), 1.71 g of aminoalkyl methacrylate copolymer E (trade name: EUDRAGIT EPO, Evonik Industries), and 1.12 g of castor oil (KOZAKAI PHARMACEUTICAL CO., LTD.) in 237.27 g of a 90-% by weight ethanol solution (a mixed liquid of ethanol 9: purified water 1). Inputted into a tumbling fluidized bed coating granulating machine (MP-01 model, Powrex Corporation) were 250 g of the core fine particles; the undercoating solution was sprayed thereto under the conditions of an inlet air temperature at 55° C. and an inlet air flow rate of 36 m³/h while the core fine particles were caused to be tumbling and flowing; and thereafter, drying was conducted, thereby obtaining undercoating spherical fine particles. Next, an overcoating solution was prepared by dispersing 26.07 g of methacrylic acid copolymer LD (trade name: EUDRAGIT L30D-55, Evonik Industries), 3.91 g of talc (Matsumurasangyo), and 0.78 g of triethyl citrate (trade name: Citroflex 2, MORIMURA BROS., INC.) in 94.16 g of purified water. Inputted into the tumbling fluidized bed coating granulating machine (MP-01 model, Powrex Corporation) were 250 g of the undercoating spherical fine particles; the overcoating solution was sprayed thereto under the conditions of an inlet air temperature at 55° C. and an inlet air flow rate of 36 m³/h while the core fine particles were caused to be tumbling and flowing; thereafter, drying was conducted; particles each having a particle diameter of 500 μm or more were removed, thereby obtaining release control fine particles (these fine particles are referred to as "Example 11 particles"). An average particle diameter of these release control fine particles calculated on a volumetric basis was 288.5 μm, and a particle diameter ratio ($D_{90}/D_{10}$) thereof with respect to particle size distribution was 2.22. In addition, an arithmetic standard deviation of the particle diameters was 99.5 μm, and a coefficient of variation in the particle diameters was 34.5%. In Example 11, the contents of the valacyclovir hydrochloride in the core fine particles and the release control particles were 92.7 wt % and 84.1 wt %, respectively.

Example 12

A liquid raw material was prepared by dissolving or suspending 2,224 g of valacyclovir hydrochloride in a solution in which 123.6 g of hydroxypropyl-cellulose (trade name: HPC-M, Nippon Soda Co., Ltd.), 10.0 g of sucralose (trade name: Sucralose P, San-Ei Gen F.F.I. Inc.), 1.2 g of thaumatin (trade name: Sunsweet T, San-Ei Gen F.F.I., Inc.), and 40.0 g of sodium chloride (Naruto Salt Mfg. Co., Ltd.) were dissolved in 10,000 g of purified water; the prepared liquid raw material was continuously sprayed into a spray drying fluidized bed granulating machine (GPCG-15 model with no inner cylinder, Powrex Corporation) under the conditions of an inlet air temperature at 85° C. and an inlet air flow rate of 6.5 m$^3$/min. from a nozzle having an orifice diameter of 1.8 mm, thereby conducting layering; drying was conducted; and thereafter, particles each having a particle diameter of 425 μm or more and 105 μm or less were removed, thereby obtaining core fine particles. An undercoating solution was prepared by dissolving 19.31 g of ethyl cellulose (trade name: ETHOCEL 45, Dow), 3.41 g of aminoalkyl methacrylate copolymer E (trade name: EUDRAGIT EPO, Evonik Industries), and 2.25 g of castor oil (KOZAKAI PHARMACEUTICAL CO., LTD.) in 474.6 g of a 90-% by weight ethanol solution (a mixed liquid of ethanol 9: purified water 1). Inputted into a tumbling fluidized bed coating granulating machine (MP-01 model, Powrex Corporation) were 500 g of the core fine particles; the undercoating solution was sprayed thereto under the conditions of an inlet air temperature at 55° C. and an inlet air flow rate of 60 m$^3$/h while the core fine particles were caused to be tumbling and flowing; and thereafter, drying was conducted, thereby obtaining undercoating spherical fine particles. Next, an overcoating solution was prepared by dispersing 54.22 g of methacrylic acid copolymer LD (trade name: EUDRAGIT L30D-55, Evonik Industries), 8.14 g of talc (Matsumurasangyo), and 1.63 g of triethyl citrate (trade name: Citroflex 2, MORIMURA BROS., INC.) in 195.9 g of purified water. Inputted into the tumbling fluidized bed coating granulating machine (MP-01 model, Powrex Corporation) were 525 g of the undercoating spherical fine particles; the overcoating solution was sprayed thereto under the conditions of an inlet air temperature at 55° C. and an inlet air flow rate of 60 m$^3$/h while the core fine particles were caused to be tumbling and flowing; drying was conducted; thereafter, particles each having a particle diameter of 500 μm or more were removed, thereby obtaining release control fine particles (these fine particles are referred to as "Example 12 particles"). An average particle diameter of these release control fine particles calculated on a volumetric basis was 329.1 μm, and a particle diameter ratio ($D_{90}/D_{10}$) thereof with respect to particle size distribution was 2.91. In addition, an arithmetic standard deviation of the particle diameters was 134.2 μm, and a coefficient of variation in the particle diameters was 40.7%. In Example 12, the contents of the valacyclovir hydrochloride in the core fine particles and the release control particles were 92.7 wt % and 84.1 wt %, respectively.

Example 13

Figure 3:
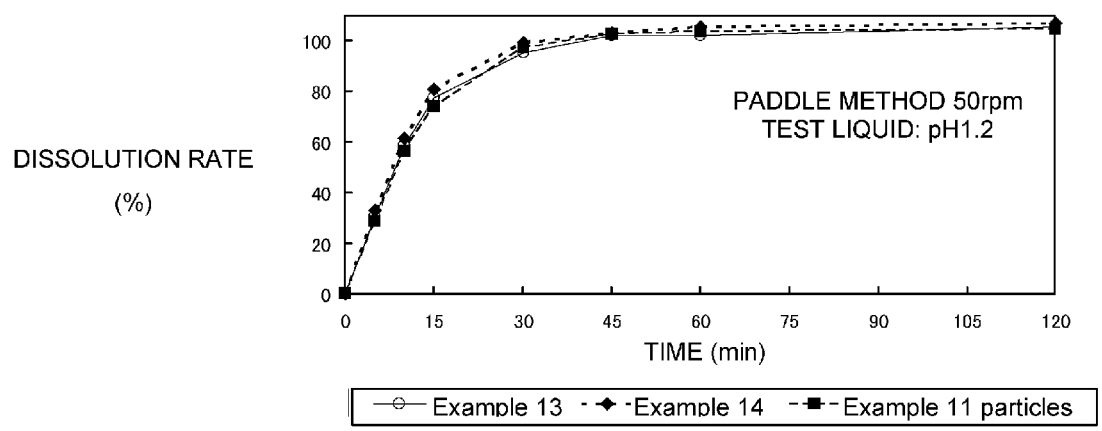
FIG. 3 a graph showing dissolution profiles of a tablet in Example 13 and a tablet in Example 14.

Inputted into a fluidized bed granulating machine (FLO-MINI, Freund Corporation) were 8.90 parts of Example 11 particles; an aqueous solution of 0.93 part of maltose (trade name: SUNMALT-GREEN, Hayashibara Co., Ltd.) and 0.02 part of thaumatin (trade name: Sunsweet T, San-Ei Gen F.F.I., Inc.) was sprayed thereto; and granulation and drying were conducted. The resultant was subjected to particle size regulation by using a No. 18 sieve (aperture: 850 μm); 0.10 part of light anhydrous silicic acid (trade name: Adsolider 101, Freund Corporation) and 0.05 part of magnesium stearate (which was from vegetable source, Taihei Chemical Industrial Co. Ltd.) were added to the obtained particle-size-regulated material and mixed therein. Tableting of the obtained mixed powder was conducted by using a desktop tableting machine (HANDTAB-200: ICHIHASHI SEIKI), using a capsule-shaped pestle having a long diameter of 18.6 mm and a short diameter of 7.3 mm, and setting a tableting pressure at 3.5 kN, thereby obtaining tablets whose mass per tablet was 880 mg and initial hardness was 20 N. Next, these tablets were preserved for 3 hours in warmed and humidified conditions at 25° C. and 75% RH by using a thermostatic and humidistatic machine (NAGANO SCIENCE CO. LTD.: LH21-11M) and thereafter, were dried by using a drying machine (PV-221, TABAI ESPEC CORP.) for 1 hour at 50° C., thereby obtaining orally disintegrating tablets. A hardness of these tablets was 253 N and an intraoral disintegrating time was 45 seconds. In addition, dissolution profiles of this tablet and Example 11 particles were the same as each other as shown in FIG. 3, and it was considered that the breakage of the film with which the particles were coated upon tableting did not occur.

Example 14

Inputted into a fluidized bed granulating machine (FLO-MINI, Freund Corporation) were 8.25 parts of Example 11 particles; an aqueous solution of 1.12 parts of maltose (trade name: SUNMALT-GREEN, Hayashibara Co., Ltd.), 0.48 part of D-mannitol (trade name: Mannite P, Mitsubishi Shoji Foodtech Co., Ltd.), and 0.02 part of thaumatin (trade name: Sunsweet T, San-Ei Gen F.F.I., Inc.) was sprayed thereto; and granulation and drying were conducted. The resultant was subjected to particle size regulation by using a No. 18 sieve (aperture: 850 μm); 0.09 part of light anhydrous silicic acid (trade name: Adsolider 101, Freund Corporation) and 0.04 part of magnesium stearate (which was from vegetable source, Taihei Chemical Industrial Co. Ltd.) were added to the obtained particle-size-regulated material and mixed therein. Tableting of the obtained mixed powder was conducted by using a desktop tableting machine (HANDTAB-200: ICHIHASHI SEIKI), using a capsule-shaped pestle having a long diameter of 18.6 mm and a short diameter of 7.3 mm, and setting a tableting pressure at 6 kN, thereby obtaining tablets whose mass per tablet was 950 mg and initial hardness was 20 N. Next, these tablets were preserved for 3 hours in warmed and humidified conditions at 25° C. and 75% RH by using a thermostatic and humidistatic machine (NAGANO SCIENCE CO. LTD.: LH21-11M) and thereafter, were dried by using a drying machine (PV-221, TABAI ESPEC CORP.) for 1 hour at 50° C., thereby obtaining orally disintegrating tablets. A hardness of these tablets was 206 N and an intraoral disintegrating time was 35 seconds. In addition, dissolution profiles of this tablet and Example 12 particles were the same as each other as shown in FIG. 3, and it was considered that the breakage of the film with which the particles were coated upon tableting did not occur.

Example 15

Inputted into a fluidized bed granulating machine (FLO-MINI, Freund Corporation) were 8.67 parts of Example 11 particles, 0.02 part of light anhydrous silicic acid (trade name: Adsolider 101, Freund Corporation), and 0.16 part of low substituted hydroxy-propylcellulose (trade name: L-HPC-NBD22, Shin-Etsu Chemical Co., Ltd.); an aqueous solution of 0.85 part of low substituted hydroxy-propylcellulose (trade name: L-HPC-NBD22, Shin-Etsu Chemical Co., Ltd.), 0.02 part of sucralose (trade name: Sucralose P, San-Ei Gen F.F.I. Inc.), and 0.02 part of thaumatin (trade name: Sunsweet T, San-Ei Gen F.F.I., Inc.) was sprayed thereto; and granulation and drying were conducted. The resultant was subjected to particle size regulation by using a No. 18 sieve (aperture: 850 μm); 0.06 part of crospovidone (trade name: Kollidon CL-SF, BASF), 0.01 part of a flavoring agent (trade name: Yoghurt Coaton DL93044, Ogawa & Co., Ltd.), 0.12 part of light anhydrous silicic acid (trade name: Adsolider 101, Freund Corporation), and 0.05 part of magnesium stearate (which was from vegetable source, Taihei Chemical Industrial Co. Ltd.) were added to the obtained particle-size-regulated material and mixed therein. Tableting of the obtained mixed powder was conducted by using a desktop tableting machine (HANDTAB-200: ICHI-HASHI SEIKI), using a capsule-shaped pestle having a long diameter of 18.6 mm and a short diameter of 7.3 mm, and setting a tableting pressure at 15 kN, thereby obtaining orally disintegrating tablets whose mass per tablet was 820 mg. A hardness of these tablets was 304 N and an intraoral disintegrating time was 31 seconds.

Example 16

Inputted into a tumbling fluidized bed coating granulating machine (MP-01 model: fluidized bed specification, Powrex Corporation) were 8.67 parts of Example 12 particles, 0.02 part of light anhydrous silicic acid (trade name: Adsolider 101, Freund Corporation), and 0.16 part of low substituted hydroxy-propylcellulose (trade name: L-HPC-NBD22, Shin-Etsu Chemical Co., Ltd.); an aqueous solution of 0.85 part of low substituted hydroxy-propylcellulose (trade name: L-HPC-NBD22, Shin-Etsu Chemical Co., Ltd.), 0.02 part of sucralose (trade name: Sucralose P, San-Ei Gen F.F.I. Inc.), and 0.02 part of thaumatin (trade name: Sunsweet T, San-Ei Gen F.F.I., Inc.) was sprayed thereto; and granulation and drying were conducted. The resultant was subjected to particle size regulation by using a No. 18 sieve (aperture: 850 μm); 0.06 part of crospovidone (trade name: Kollidon CL-SF, BASF), 0.01 part of a flavoring agent (trade name: Yoghurt Coaton DL93044, Ogawa & Co., Ltd.), 0.12 part of light anhydrous silicic acid (trade name: Adsolider 101, Freund Corporation), and 0.05 part of magnesium stearate (which was from vegetable source, Taihei Chemical Industrial Co. Ltd.) were added to the obtained particle-size-regulated material and mixed therein by using a V-type rotary powdered medicine mixer (VT-2V model, Takizawa Medical Industry Co., Ltd.). Tableting of the obtained mixed powder was conducted by using a rotary-type tableting machine (VIRG-0512, KIKUSUI SEISAKUSHO LTD.), using a capsule-shaped pestle having a long diameter of 18.6 mm and a short diameter of 7.3 mm, and setting a tableting pressure at 15 kN, thereby obtaining orally disintegrating tablets whose mass per tablet was 820 mg. A hardness of these tablets was 277 N and an intraoral disintegrating time was 35 seconds.

The invention claimed is:
1. Functional drug-containing particles comprising: substantially spherical drug-containing particles essentially including drug particles and a binder; and a film of a functional polymer selected from the group consisting of an enteric polymer, a release control polymer, and a bitter taste masking polymer coating said drug-containing particles, the functional drug-containing particles having an average particle diameter of 400 μm or less,
the substantially spherical drug-containing particles being manufactured from a solution of the binder including dissolved or suspended drug by using a spray drying fluidized bed granulation apparatus.
2. The functional drug-containing particles according to claim 1, wherein the functional drug-containing particles have broad particle size distribution, a particle diameter ratio $D_{90}/D_{10}$ of the functional drug-containing particles with respect to particle size distribution calculated on a volumetric basis being 1.65 or more, or a coefficient of variation in particle diameters being 24% or more.
3. The functional drug-containing particles according to claim 1, wherein a common auxiliary component is mixed, and the functional drug-containing particles have sufficient elasticity which allows the functional drug-containing particles to be molded into a tablet including at least 50% by weight of the functional drug-containing particles through compression molding.
4. The functional drug-containing particles according to claim 1, wherein drug-containing particles including at least 70% by weight of the drug particles are coated with the functional polymer film, and a drug content is at least 40% by weight or more.
5. The functional drug-containing particles according to claim 1, wherein the binder is hydroxypropyl-cellulose, hydroxypropyl methyl cellulose, a homopolymer or copolymer of vinylpyrrolidone, polyvinyl alcohol, or ethyl cellulose.
6. The functional drug-containing particles according to claim 1, wherein an average particle diameter of the drug particles is 10 μm or less.
7. The functional drug-containing particles according to claim 1, wherein a particle diameter of each of the drug-containing particles is larger than 105 μm.
8. The functional drug-containing particles according to claim 1, wherein the drug is ambroxol hydrochloride, and the functional film is the release control film.
9. The functional drug-containing particles according to claim 1, wherein the drug is a valacyclovir hydrochloride, and the functional film is the bitter taste masking film.
10. A method for manufacturing the functional drug-containing particles according to claim 1, comprising:
a) manufacturing substantially spherical drug-containing particles directly from a solution of a binder including dissolved or suspended drug by using a spray drying fluidized bed granulation apparatus; and
b) forming a film by coating the obtained drug-containing particles with a functional polymer selected from the group consisting of an enteric polymer, a release control polymer, and a bitter taste masking polymer.
11. The method for manufacturing the functional drug-containing particles according to claim 10, wherein a) includes spraying the solution of the binder including the drug upward from a bottom portion of the apparatus toward a central portion of the apparatus.
12. A tablet comprising the functional drug-containing particles according to claim 1 and an auxiliary component for the tablet, a content of the functional drug-containing particles being at least 50% by weight, the tablet having a hardness of at least 40 N.
13. The tablet according to claim 12, wherein the tablet is an orally disintegrating tablet.

14. A method for manufacturing a tablet, comprising:
adding at least a disintegrating agent and a lubricant to the functional drug-containing particles according to claim 1; and
subjecting the resultant to compression molding.

15. A method for manufacturing a tablet, comprising:
mixing and kneading the functional drug-containing particles according to claim 1 in an aqueous solution including a binder and sugar or sugar alcohol;
molding the wet kneaded substance into a tablet shape; and
thereafter, drying the wet molding.

16. A method for manufacturing a tablet, comprising:
coating the functional drug-containing particles according to claim 1 with a saccharide or sugar alcohol capable of becoming amorphous;
thereafter, subjecting the coated substance to compression molding under a pressure of 5 kN/cm$^2$ or less to mold into the tablet; and
by humidifying and drying the molded tablet, converting an amorphous state of the saccharide to a crystalline state of the saccharide.

17. The method for manufacturing a tablet according to claim 14, wherein the tablet is an orally disintegrating tablet.

\* \* \* \* \*